(12) United States Patent
Liljegren et al.

(10) Patent No.: US 11,039,926 B2
(45) Date of Patent: Jun. 22, 2021

(54) VALVE PLANNING TOOL

(71) Applicant: SPIRATION, INC., Redmond, WA (US)

(72) Inventors: Erik Liljegren, Redmond, WA (US); Xavier Gonzalez, Redmond, WA (US); Lauri Devore, Redmond, WA (US); Fan Zhang, Redmond, WA (US)

(73) Assignee: SPIRATION, INC., Redmond, WA (US)

( * ) Notice: Subject to any disclaimer, the term of this patent is extended or adjusted under 35 U.S.C. 154(b) by 246 days.

(21) Appl. No.: 16/079,809

(22) PCT Filed: Jan. 30, 2017

(86) PCT No.: PCT/US2017/015636
§ 371 (c)(1),
(2) Date: Aug. 24, 2018

(87) PCT Pub. No.: WO2017/164984
PCT Pub. Date: Sep. 28, 2017

(65) Prior Publication Data
US 2019/0053906 A1    Feb. 21, 2019

Related U.S. Application Data

(60) Provisional application No. 62/313,431, filed on Mar. 25, 2016.

(51) Int. Cl.
*A61F 2/24* (2006.01)
*A61B 5/08* (2006.01)
(Continued)

(52) U.S. Cl.
CPC .............. *A61F 2/2496* (2013.01); *A61B 5/08* (2013.01); *A61B 5/1076* (2013.01);
(Continued)

(58) Field of Classification Search
CPC .............. A61F 2/2496; A61F 2240/005; A61F 2002/043; A61F 2/2433; A61B 5/08;
(Continued)

(56) References Cited

U.S. PATENT DOCUMENTS 5,365,331 A   11/1994  Tamburrino et al.
6,428,512 B1   8/2002  Anderson et al.
(Continued)

FOREIGN PATENT DOCUMENTS

EP      2801387 A1   11/2014
WO   2004006767 A2    1/2004
(Continued)

OTHER PUBLICATIONS

International Search Report, PCT/US2017/015636 (WO2017/164984) dated Mar. 3, 2017.

*Primary Examiner* — Brian A Dukert
*Assistant Examiner* — Rebecca Lynee Zimmerman
(74) *Attorney, Agent, or Firm* — Clements Bernard Walker; Alistair K. Chan

(57) ABSTRACT

A valve planning tool comprising: (a) a stem having a distal end and a proximal end, (b) an anchor indicator located at the distal end, and (c) a balloon located proximal of the anchor indicator, the balloon including: (i) a retracted state and (ii) a deployed state; wherein the balloon is inflatable from the retracted state to the deployed state and the balloon is substantially non-compliant so that the balloon is only inflatable to one size.

13 Claims, 4 Drawing Sheets

(51) Int. Cl.
*A61B 5/107* (2006.01)
*A61B 5/00* (2006.01)

(52) U.S. Cl.
CPC ...... *A61B 5/6867* (2013.01); *A61F 2240/005* (2013.01); *A61F 2250/0073* (2013.01)

(58) Field of Classification Search
CPC . A61B 5/1076; A61B 5/107; A61B 2017/242; A61G 13/1215
See application file for complete search history.

(56) References Cited

U.S. PATENT DOCUMENTS

| | | |
|---|---|---|
| 6,524,259 B2 | 2/2003 | Baxter-Jones et al. |
| 7,527,601 B2 | 5/2009 | Dubey et al. |
| 7,654,979 B2 | 2/2010 | Simpson |
| 7,713,216 B2 | 5/2010 | Dubey et al. |
| 7,749,176 B2 | 7/2010 | Dubey et al. |
| 7,811,239 B2 | 10/2010 | Dubey et al. |
| 7,854,228 B2 | 12/2010 | Wilson et al. |
| 8,357,139 B2 | 1/2013 | Deem et al. |
| 9,872,755 B2 | 1/2018 | Olivera et al. |
| 2001/0039388 A1 | 11/2001 | Korotko et al. |
| 2003/0070682 A1 | 4/2003 | Wilson |
| 2003/0216769 A1 | 11/2003 | Dillard et al. |
| 2004/0059263 A1* | 3/2004 | DeVore ................ A61B 5/1076 600/587 |
| 2006/0064039 A1 | 3/2006 | Griego et al. |
| 2007/0083126 A1 | 4/2007 | Marko et al. |
| 2008/0072914 A1 | 3/2008 | Hendricksen et al. |
| 2010/0198346 A1 | 8/2010 | Keogh |
| 2011/0065982 A1 | 3/2011 | Wibowo et al. |
| 2011/0245859 A1* | 10/2011 | Klaiman ............... A61B 5/1076 606/192 |
| 2012/0035540 A1 | 2/2012 | Ferren et al. |
| 2012/0149978 A1 | 6/2012 | Olivera et al. |
| 2013/0131710 A1* | 5/2013 | Carmeli ................ A61M 29/02 606/194 |
| 2014/0336617 A1 | 11/2014 | Schaeffer |

FOREIGN PATENT DOCUMENTS

| | | |
|---|---|---|
| WO | 2015153493 A1 | 10/2015 |
| WO | 2015153495 A1 | 10/2015 |
| WO | 2015153500 A1 | 10/2015 |

* cited by examiner

VALVE PLANNING TOOL

FIELD

The present teachings generally relate to a valve planning tool for sizing a passageway for a mechanical airway valve.

BACKGROUND

The present teachings are predicated upon providing a valve planning tool that allows a user to measure a passageway and preferably an airway so that a valve can be selected for use in the airway. Currently, passageways are measured using balloons that are inflated using a non-compressible fluid such as saline until the balloon fills the passageway. During filling of the balloon air is bled from the balloon to ensure that a proper measurement and proper sealing by the valve will be achieved. Over inflation or under inflation of the balloon also are monitored during filling. The amount of fluid placed in the balloon during sizing is then compared to a sizing chart to determine the proper sized valve to seal a given airway. While this process is very effective at measuring passageways, the process may have to be repeated one or more times in order to ensure that a correctly sized valve is selected for a given passageway and bleeding the balloon may extend the procedure. An example of such a device and method is available from Spiration at http://www.spiration.com//sites/default/files/pagefiles/PI-03175AB_ASK_IFU-HUD_WEB.pdf last accessed on Feb. 15, 2016 the teachings of which are expressly incorporated by reference herein in their entirety for all purposes. An example of another device is sold under the name Aero Sizer by Merit Medical Endotek, the teachings of which are expressly incorporated by reference herein for all purposes.

Other passageways are measured using electronic sizing devices that are expanded into contact with a wall of a passageway and a digital read out is provided. An example of a sizing device is found in U.S. Pat. No. 8,357,139 the teachings of which are expressly incorporated by reference herein in their entirety for all purposes.

Other devices are conformable to the size of the airway such that the airway does not need to be measured and a one size fits all device may be employed. However, if the size of the device is not selected properly or the device is not set in the airway, the device may be expelled (e.g., coughed out) or may move within the passageway such that the effectiveness of the device is reduced. An example of such a device is found in U.S. Pat. No. 7,854,228 the teachings of which are expressly incorporated by reference herein in their entirety for all purposes.

Examples of other sizing device may be found in U.S. Patent Application Publication No. 2012/0149978; and International Patent Application Publication No. WO2015/153493 the teachings of which are all incorporated by reference herein in their entirety for all purposes.

It would be attractive to have a sizing device that accurately measures a cross-sectional length of a passageway. It would be attractive to have a sizing device that measures non-round passageways so that a valve can be selected that will seal the passageway and remain in place. What is needed is a planning tool that allows a user to measure both a cross-sectional length and an axial length of a passageway at the same time without any repositioning of the valve planning tool. What is needed is a valve planning tool that indicates if a passageway is one size or more larger than the valve planning tool and/or one size or more smaller than the valve planning tool.

SUMMARY

The present teachings meet one or more (if not all) of the present needs by providing an apparatus comprising: valve planning tool comprising: (a) a stem having a distal end and a proximal end, (b) an anchor indicator located at the distal end, and (c) a balloon located proximal of the anchor indicator, the balloon including: (i) a retracted state and (ii) a deployed state; wherein the balloon is inflatable from the retracted state to the deployed state and the balloon is substantially non-compliant so that the balloon is only inflatable to one size.

The present teachings provide a kit comprising: two or more valve planning tools of the teachings herein.

A method comprising: (1) compacting the valve planning tool of the teachings herein into a retracted state, and (2) inserting the valve planning tool into a working channel of a bronchoscope.

The present teachings provide a sizing device that accurately measures a cross-sectional length of a passageway. The present teachings provide a sizing device that measures non-round passageways so that a valve can be selected that will seal the passageway and remain in place. The present teachings provide a planning tool that allows a user to measure both a cross-sectional length and an axial length of a passageway at the same time without any repositioning of the valve planning tool. The present teachings provide a valve planning tool that indicates if a passageway is one size or more larger than the valve planning tool and/or one size or more smaller than the valve planning tool.

DETAILED DESCRIPTION

Figure 1A:
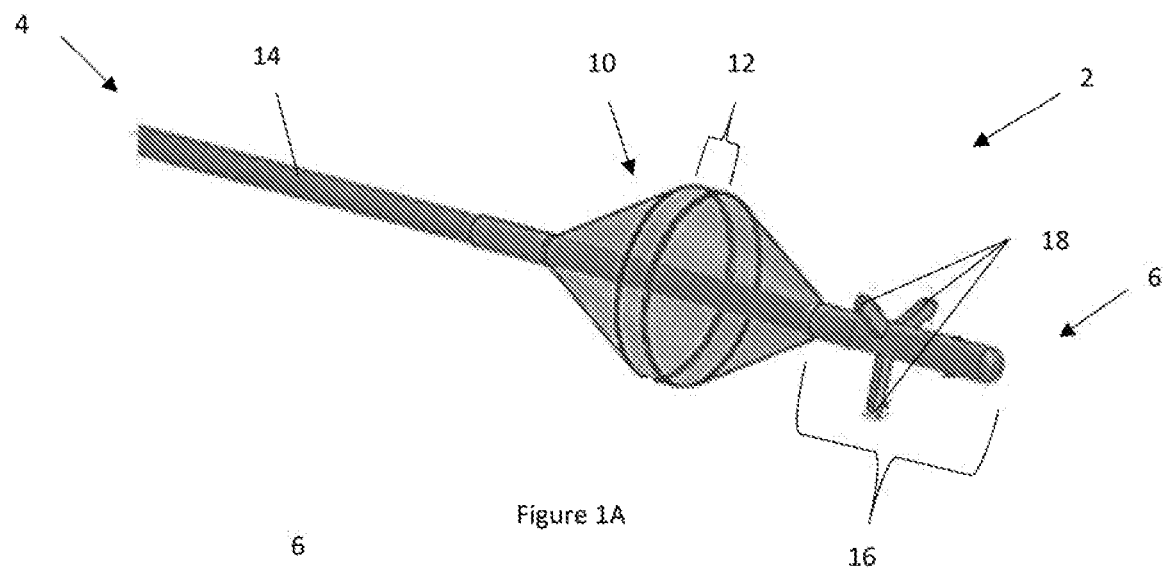
FIG. 1A illustrates an perspective view of a valve planning tool.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are directed to an improved valve planning tool. The valve planning tool functions to measure one or more cross-sectional lengths of a structure. The valve planning tool may measure one or more diameters of a structure. Preferably, the structure is a passageway and more preferably the structure is an airway. Preferably, the valve planning tool measures a plurality of cross-sectional lengths (e.g., diameter) of a passageway. More preferably, the valve planning tool measure a passageway to determine which valve can seal the passageway. For example, the passageway may measure a length of a passageway from one side to the other despite the passageway being non-circular or irregular in shape. If the passageway is circular then the cross-sectional length is a diameter. The valve planning tool may function to measure an axial length of a passageway. The valve planning tool may measure if there are any obstructions within a given axial length that would affect a valve from deploying, being retained in a location, sealing, or a combination thereof. Preferably, the valve planning tool allows a user to simultaneously measure one or more cross-sectional lengths and one or more axial lengths of a passageway. The axial length is a length of the valve or valve planning tool from a distal end to a proximal end. The axial length may be a distance that the valve spans when retracted, deployed, or both.

The valve planning tool in a retracted state may fit within a delivery catheter, a sheath, or a channel of a bronchoscope. Preferably, the valve planning tool in a retracted tool will fit within a bronchoscope. The valve planning tool may have a balloon that is inflatable and deflatable. The valve planning tool may have one or more tangs that are expandable and retractable. The valve planning tool may have dimensions that mirror those of a valve. Preferably, the valve planning tool has a dimension (i.e., length) that is equal to a distance that a delivery catheter extends into a passageway. The valve planning tool may have a length that simulates a total length that the delivery catheter extends into a passage during deployment or pre-deployment. The valve planning tool may have a length of about 8 mm or more, about 10 mm or more, about 11 mm or more, about 12 mm or more when measured from the seal area indicator to the tangs. The valve planning tool may have a length of about 20 mm or less, about 15 mm or less, or about 13 mm or less. The valve planning tool may be compressed (in a retracted state) to fit within the bronchoscope and may expand (in a deployed state) to substantially fill a length of a passageway such as an airway or a branch of bronchia or a bronchiole.

The deployed state may have the balloon partially or fully inflated. The deployed state may have one or more tangs extending radially outward from the stem. The deployed state may have all of the tangs extending radially outward from the stem and the balloon inflated so that the balloon is substantially in contact with a wall of a passageway. The valve planning tool may be moved from the deployed state back into the retracted state so that the valve planning tool may be removed. The valve planning tool may be retracted from the proximal end to the distal end.

The proximal end may be an end of the valve planning tool closest to a user, an opening of a passageway, or both. The proximal end may function to size a sealing area of a valve. The largest cross-sectional length of the valve planning tool may be located at the proximal end. The proximal end may include one or more balloons. The proximal end may be located opposite a distal end. The distal end may be located the farthest into a passageway. The distal end may include one or more anchor indicators. The distal end may extend beyond a location of where a distal end of a valve may extend (e.g., a length indicator of the anchor indicator may extend distal of the tangs). The distal end may extend to a location where the delivery catheter extends. A stem may extend from the proximal end to the distal end.

The stem functions to carry the balloon and anchor indicator so that a passageway can be measured. The stem may be a longitudinal axis of the valve planning tool. The stem may be rigid. The stem may be flexible. The stem may be solid. The stem may be hollow. The stem may be made of plastic, metal, a bio-compatible material, or a combination thereof. The stem may have one or more components that extend through the stem. The stem may be used to move (e.g., push) the valve planning tool into place. The stem may be used to move (e.g., pull) the valve planning tool out of the passageway. The stem may include one or more fluid conduits that extend from the proximal end to the distal end. The stem may include one or more actuator devices (e.g., wires, strings, cables) that may extend through a length of the stem. The stem may include one or more fluid conduits that extend through the stem and into the balloon.

The one or more balloons may function to measure a cross-sectional length of a passageway. Preferably, the one or more balloons function to measure a sealing area in a passageway. More preferably, a single balloon measures a sealing area at a single location. The balloon is expandable and contractible. The balloon may have a portion that moves along the length of the stem. The balloon may be manipulated by an actuator device. The balloon may be manipulated by an actuator device that extends through the stem. The balloon may be fixedly connected to the stem. The balloon may be elastically deformable. Preferably, the balloon is not elastically deformable (i.e., the balloon may only expand to a predetermined size). The balloon may conform to non-round shapes. The balloon may be made of a non-compliant material or a semi-compliant material. The balloon in the deployed state, may be made of polyethylene terephthalate, polyester, a thermoplastic, polypropylene, polyether, a polyether block amide, polyamide, polyester, polyurethane, a minimally-stretchable plastic, a minimally-stretchable bio-compatible plastic, a non-elastic plastic, a non-stretchable plastic, or a combination thereof. The balloon may be deployed using any fluid. The balloon may be deployed using a compressible fluid (e.g., air) or a non-compressible fluid (e.g., saline). The balloon may mirror the shape of the valve. The balloon may have a shape that is spherical, egg shaped, one or more cones, one or more pyramids, one or more pentagons, diamond shape, oval, round shaped, kite shaped, two back to back pyramids, or a combination thereof. The balloon, in the deployed state, may have a location along the length where the balloon is farthest from the stem. The balloon, in the deployed state, may gradually increase in distance from the stem, gradually decrease in distance from the stem, or both. The balloon may have one or more segments that run parallel to the stem. The balloon may be two back to back shapes. For example, the balloon may be two cones that are back to back with a linear segment connecting the cones. The linear segment may be a seal area indicator.

Seal area indicator may function to indicate a sealing location of a valve. The seal area indicator may function to align a delivery catheter with an area of interest. The valve planning tool, the delivery catheter, or both may include a seal area indicator. The seal area indicator of the delivery catheter may ensure that the seal area of a valve aligns with the location measured by the seal area indicator of the valve planning tool. The seal area indicator may measure a sealing location of a valve. The seal area indicator may have a length that is substantially the same as an area to be sealed by a valve. The cross-sectional length of the seal area indicator of the valve planning tool may be substantially identical to the cross-sectional length of the valve (i.e., the difference may be about 1 mm or less, preferably about 0.5 mm or less, or more preferably about 0.25 mm or less). The seal area indicator of the valve planning tool may have a maximum diameter. The seal area indicator of the valve planning tool may indicate how the valve will seal a non-round shape, an irregular shape, or both. The seal area indicator of the valve planning tool may indicate how a range of cross-sectional lengths will seal. The seal area indicator may be at a proximal end of the seal area indicator, indicate a proximal end of a valve, or both. The seal area indicator of the valve planning tool may indicate a maximum size (e.g., diameter) that a valve can seal. The seal area indicator of the valve planning tool may have a largest cross-sectional length of about 4 mm or more, about 5 mm or more, about 6 mm or more, about 7 mm or more, or about 9 mm or more. The seal area indicator of the valve planning tool may have a largest cross sectional length of about 12 mm or less or about 10 mm or less. The seal area indicator may be used in conjunction with an anchor indicator to determine the best size valve to use for a site of a passageway.

The anchor indicator may function to determine if the anchors of the valve can open. The anchor indicator may function to measure a minimum size passageway that a valve may seal. The anchor indicator may function to measure both the minimum size and maximum size a valve can be sealed. The anchor indicator may function to measure a maximize size valve that the valve can seal. The anchor indicator may function to measure the passageway for a maximum cross-sectional length of next size down or a minimum cross-sectional length of a next size up valve relative to the cross-sectional length being measured using the balloon. The anchor indicator may have a cross-sectional length of about 6 mm or more, about 8 mm or more, about 9 mm or more, about 10 mm or more, or about 11 mm or more. The anchor indicator may have a cross-sectional length of about 20 mm or less, about 18 mm or less, about 15 mm or less, about 13 mm or less, or about 12 mm or less. The anchor indicator may function to measure an axial length that a delivery catheter may extend into a passageway. The anchor indicator may have a portion that extends distal beyond the tangs (i.e., a length indicator). The length indicator may extend beyond the tangs. The length indicator may extend beyond the location of the anchors of the valve, in the deployed state, so that the anchor indicator indicates the distance (e.g., axial length): the valve delivery catheter extends beyond the end of the valve during deployment, the length of the anchors when extended distally, or both. The length indicator may indicate the length of the valve in the deployed state. The length indicator may indicate the length of the valve in the retracted state. The anchor indicator may indicate a total length of the valve plus a delivery catheter during deployment. A length of the valve planning tool from the seal area indicator to the distal end of the anchor indicator is equal to the length of valve plus the length of a delivery catheter needed to deploy the valve. The length of the length indicator distally beyond the tangs may be about 1 mm or more, about 2 mm or more, or about 3 mm or more. The length of length indicator beyond the tangs may be about 10 mm or less, about 8 mm or less, or about 5 mm or less. The anchor indicator may include one or more tangs and preferably a plurality of tangs that extend radially outward.

The tangs may function to measure if anchors of the valve can move from a retracted state to a deployed state. The tangs may function to measure a minimum passageway that a valve can seal. The tangs may function to measure a maximum passageway that a valve can seal. The tangs may extend radially outward from a stem. The tangs may all be the same length. The length of the tangs may vary. For example, some tangs may have a length that is equal to a minimum size (minor tangs) that a valve can seal and other tangs may have a length that is equal to a maximum size (major tangs) that a valve can seal. The valve planning tool may have two or more tangs, three or more tangs, four or more tangs, or even five or more tangs. The valve planning tool may have one or more minor tangs and preferably two or more minor tangs. The valve planning tool may have one or more major tangs and preferably two or more major tangs. The minor tangs and the major tangs may be located an angle apart from each other. The major tangs and minor tangs; two major tangs, two minor tangs; or a combination of major tangs and minor tangs may be located apart by about 180 degrees or less, about 135 degrees or less, about 120 degrees or less, or even about 105 degrees or less (e.g., each of the tangs may be located about 90 degrees apart when there are four tangs). The major tangs and minor tangs; two major tangs, two minor tangs; or a combination of major tangs and minor tangs may be located apart by about 25 degrees or more, about 45 degrees or more, or about 75 degrees or more. The tangs may have a length that indicates if the valve anchors can open. The tangs may have a length that indicates if the valve anchors can contact the passageway. The one or more tangs may be static (i.e., open in the retracted state). The one or more tangs may be resilient so that the tangs move to an open or free state. A length of the valve planning tool from the tangs to the seal area indicator may indicate the length of the valve. The tangs may be used to measure a passageway.

The passageway may be any passageway in a lung. The passageway may be a trachea, a bronchi, bronchiole, a branch of a bronchi, a branch of a bronchiole, or a combination thereof. The passageway may be any passageway that may be sealed by a valve to control airflow. The valve may include an anchor, a plurality of struts, a plurality of anchors, a membrane, a seal area, or a combination thereof. Examples, of exemplary valves that the present teachings may be used with are found in U.S. Pat. Nos. 8,647,392; 7,942,931; and 7,533,671 the teachings of with are expressly incorporated by reference herein for all purposes regarding a valve and its components. The anchor may hold the valve in place upon deployment. The struts may expand radially outward and contact a wall of a passageway. The struts may extend outward and open a membrane. The membrane may prevent airflow from extending past the valve. The valve and valve planning tool may be included individually or together in a kit.

The kit may include one or more of the valve planning tools of the teachings herein. The kit may include one or more valves. The kit may include one valve planning tool for each of the valves that may be used. The kit may include an inflation syringe. The kit may include a measuring device. The kit preferably includes two or more valve planning tools, three or more valve planning tools, and four or more valve planning tools. The kit may include an instructions manual. The kit may include one or more valve planning tools, two or more valve planning tools, three or more valve planning tools, or even four or more valve planning tools. When the kit includes more than one valve planning tool the valve planning tools are all a different size. Preferably, the kit includes the same number of valve planning tools as there are available valve sizes.

The valve planning tool may be used in a method that may employ one or more of the steps herein that may be employed in virtually any order. A method may be employed to size a passageway. The method may include a step of loading the valve planning tool in a delivery catheter. The method may include a step of retracting the valve planning tool. The method may include a step inserting the delivery catheter into a passageway. Retracting the delivery catheter. Moving the valve planning tool into the passageway. Inflating the balloon of the valve planning tool. Visually inspecting the balloon, the tangs, the seal area indicator, or a combination thereof. The visual inspection may include moving the imaging device around the outside of the valve planning tool to inspect the seal area. The visual inspection may be performed when the tangs are being inserted. The visual inspection may be performed during inflation. The visual inspection compares the valve planning tool to the structure to determine if the valve can seal the structure (i.e., passageway). Determining the size of the valve. Removing the valve planning tool. Inserting a second valve planning tool or a third valve planning tool into the passageway and repeating the steps taught herein.

FIG. 1A illustrates a perspective view of a valve planning tool 2 including a stem 14. The stem 14 includes a distal end 6 and a proximal end 4. The distal end 6 of the stem 14 includes an anchor indicator 16 with a plurality of tangs 18. A balloon 10 is located between the distal end 6 and the proximal end 4 and is proximal of the anchor indicator 16. The balloon 10 is non-compliant and when inflated, indicates the maximum airway size that a valve (not shown) can occlude/seal. The balloon 10 includes a seal area indicator 12 that represents a contact location of a valve (not shown).

Figure 1B:
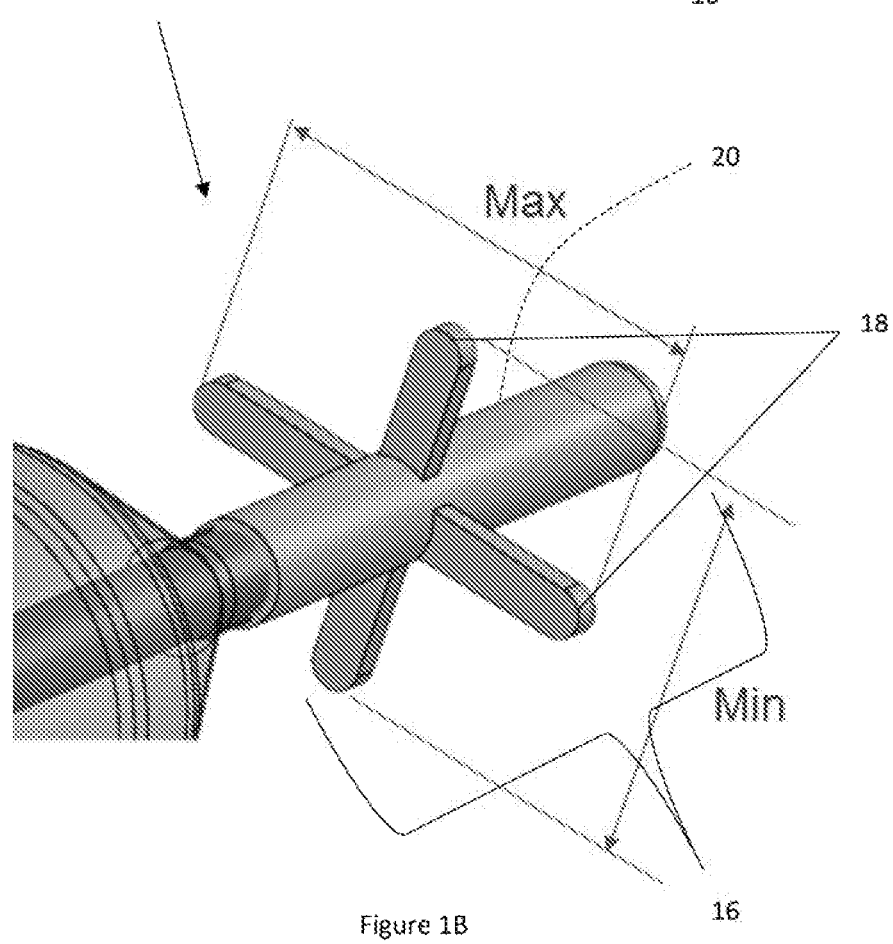
FIG. 1B illustrates a close-up view of a distal end of a valval planning tool.

FIG. 1B illustrates a close-up view of a distal end 6. The distal end 6 includes an anchor indicator 16 with a plurality of tangs 18 that extend radially outward. As shown, the tangs 18 have one direction that indicates a minimum dimension that a sealing area of an associated valve (not shown) can seal, and tangs 18 in a second direction indicate a maximum dimension that a sealing area (not shown) of an associated valve can seal. The anchor indicator 16 a length indicator 20 that extends beyond the tangs 18 and measures the total length needed to insert a delivery catheter (not shown) to deploy a valve (not shown).

Figure 1C:
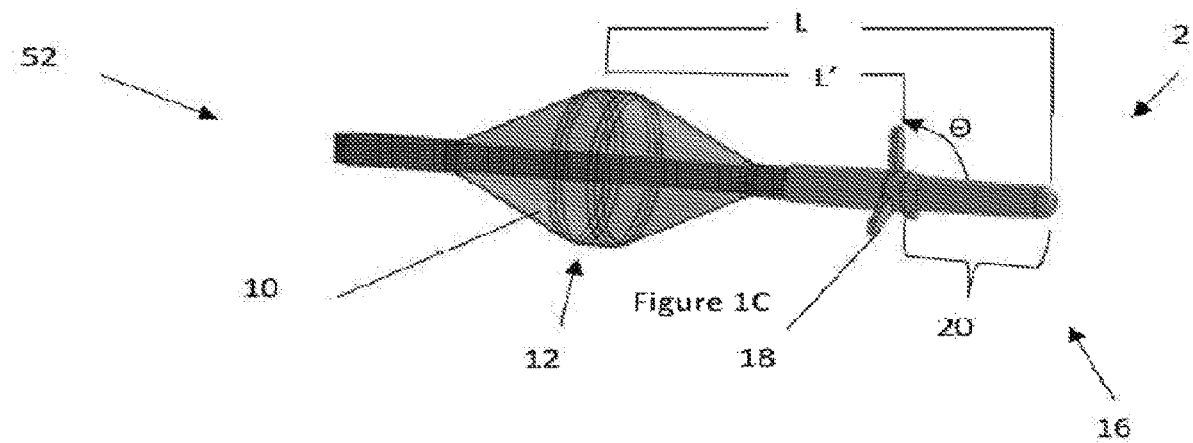
FIG. 1C illustrates a close-up view of the seal area indicator and anchor indicator of a valve planning tool.

FIG. 1C illustrates a side view of a valve planning tool 2 with a balloon 10 in a deployed state 52. The balloon 52 has a seal area indicator 12 that indicates the location of contact between an anatomical feature and the valve (not shown). The valve planning tool 2 has a length (L) that represents the length that a delivery catheter (not shown) extends into a passage way beyond the seal area indicator 12 of the valve planning tool 2. The length (L') is the total length of the valve (not shown) in the deployed state when the anchors are moved into contact with the anatomical feature. At the distal end of the valve planning tool are a plurality of tangs 18 that extend radially outward. The tangs 18 have a length that measures for the angle (Θ) of the anchor swing so that the anchors of the valve (not shown) can move from a retracted state to a deployed state. The anchor indicator 16 also includes a length indicator 20 that extends distally beyond the tangs 18.

Figure 2:
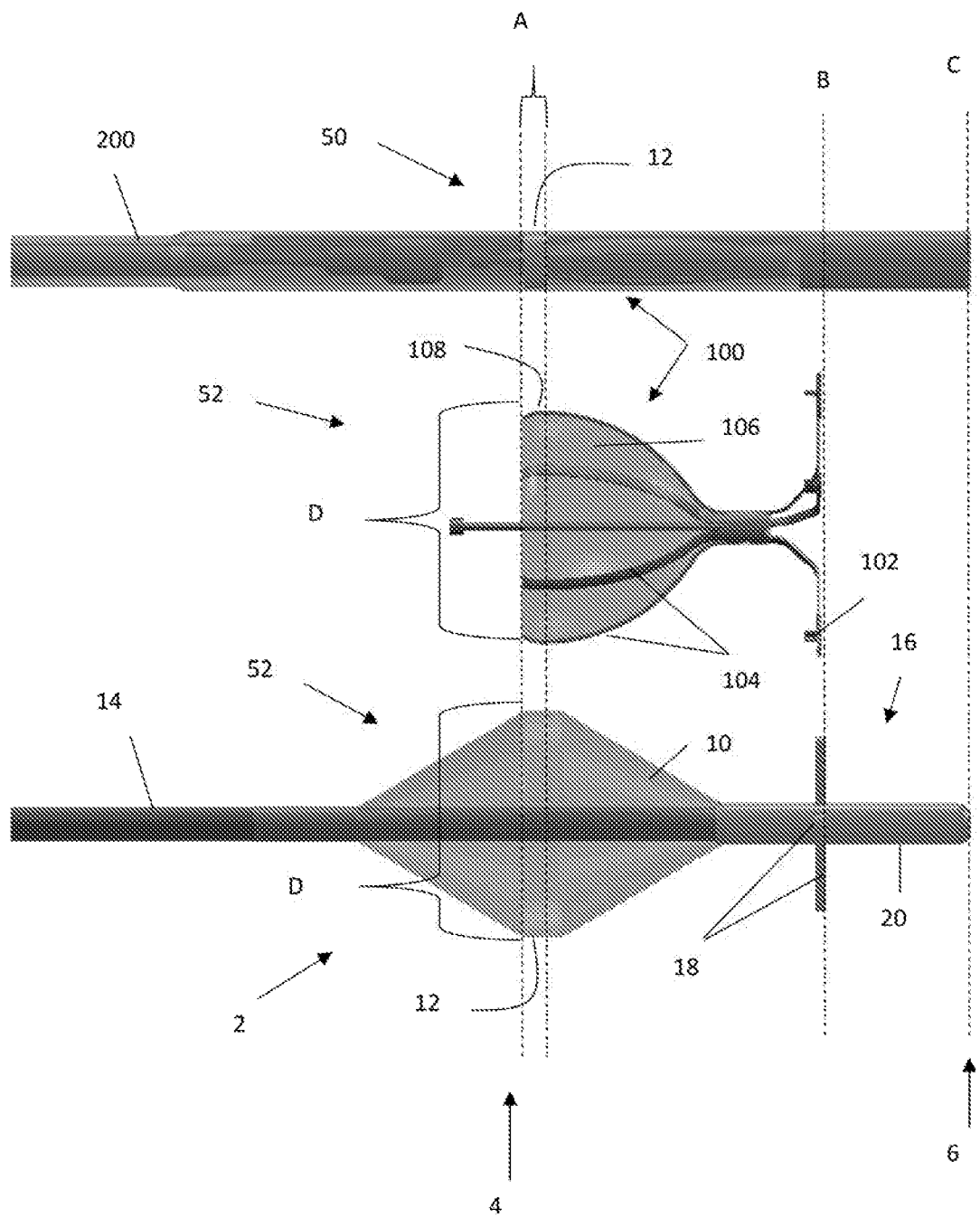
FIG. 2 illustrates a comparison of a valve planning tool and a valve in a retracted and deployed state.

FIG. 2 illustrates: (1) a valve planning tool 2 in the deployed state 52 that is aligned with (2) a valve 100 in the retracted state (inside the valve delivery catheter) 50 and (3) a valve 100 in the deployed state 52 to demonstrate the features that the valve planning tool 2 are simulating. The valve planning tool 2 includes a stem 14 and has a balloon 10 with a proximal end 4 and a distal end 6. The proximal end 4 has a seal area indicator 12 that measures an airway (not shown) so that the seal area indicator 12 indicates if the seal area 108 of the valve 100 in the deployed state 52 will seal an airway. The seal area indicator 12 also indicates where the seal area 108 will longitudinally align in both the retracted state 50 and the deployed state 52. The seal area indicator 12 of the delivery catheter 200 assists a user in longitudinally aligning the valve 100 with the area to be sealed that was measured by the valve planning tool 2. The valve 100 is moved into alignment with the seal area 108 so that the valve 100 aligns with the measured area as is indicated by the lines (A). The seal area 108 of the deployed valve 100 and the seal area indicator 12, when inflated, have the same diameter (D) so that the seal area indicator 12 demonstrates that the valve 100 can seal an airway (not shown) when the valve is fully deployed. The seal area indicator 12 indicates the proximal end 4 of the valve 100 although the valve planning tool 2 has some balloon 10 that extends beyond the seal area indicator 12. The balloon 10 of the valve planning tool 2 tapers downward towards the stem 14 so that the balloon 10 generally mirrors the shape of the struts 104 and membrane 106. The valve planning tool 2 includes an anchor indicator 16 with tangs 18 that measure the cross-sectional length of the airway (not shown) to ensure that the anchors 102 of the valve 100 can open and will contact the walls of the airway, and the tangs 18 represent the minimum size that the seal area 108 of the valve 100 can seal. The tangs 18 align with the anchors 102 in the deployed state along line (B) as is shown. The anchor indicator 16 has a length indicator 20 that extends distal of the tangs 18 that represents the approximate swing of the anchors 102 to ensure that the anchors 102 can deploy and to ensure that the delivery catheter 200 can fully extend into the airway (not shown) so that the delivery catheter 200 (e.g., bronchoscope) can be retracted while the valve 100 is deployed in a predetermined location. The distal end 6 of the delivery catheter 200 extends out of a bronchoscope (not shown) and the anchor indicator 16 are aligned as shown by line (C).

Figure 3:
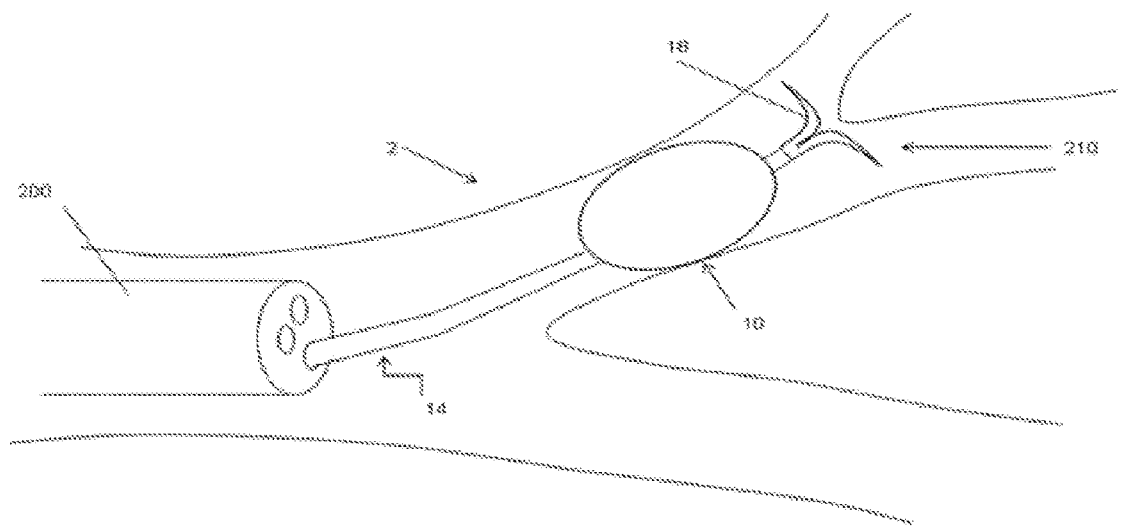
FIG. 3 illustrates a valve planning tool located within a passageway.

FIG. 3 illustrates a catheter 200 (e.g., bronchoscope) with the valve planning tool being extended into an airway 210. The valve planning tool 2 is extending out of the end of the bronchoscope 200 by the stem 14, and the balloon 10 is expanded to fill the air way 210. The tangs 18 extend outward to show where the valve anchors will end up if deployed.

Figure 4A:
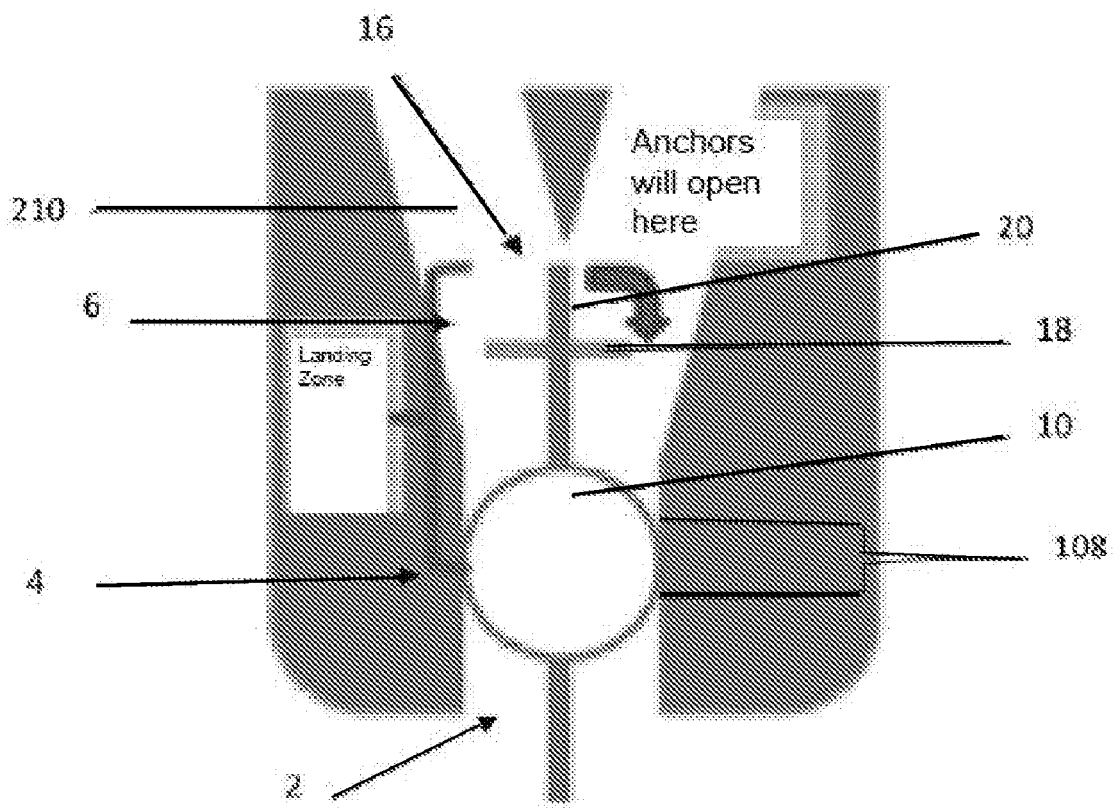
FIG. 4A illustrates a plan view of a valve planning tool in a passageway.

FIG. 4A illustrates the valve planning tool 2 located within an airway 210 to measure the airway 210. The balloon 10 of the valve planning tool 2 is inflated so that the walls of the balloon 10 are in contact with the walls of the airway 210 at a seal area 108. The seal area 108 represents a proximal end 4 of a valve (not shown) and the tangs 18 represent a distal end 6 of the valve planning tool 2. The distal end 6 (which aligns with the distal end of the valve) of the valve planning tool 2 includes an anchor indicator 16 with a length indicator 20 that is used to determine that the catheter (not shown) can be fully inserted into the airway 210 and that the anchors (not shown) can fully open.

Figure 4B:
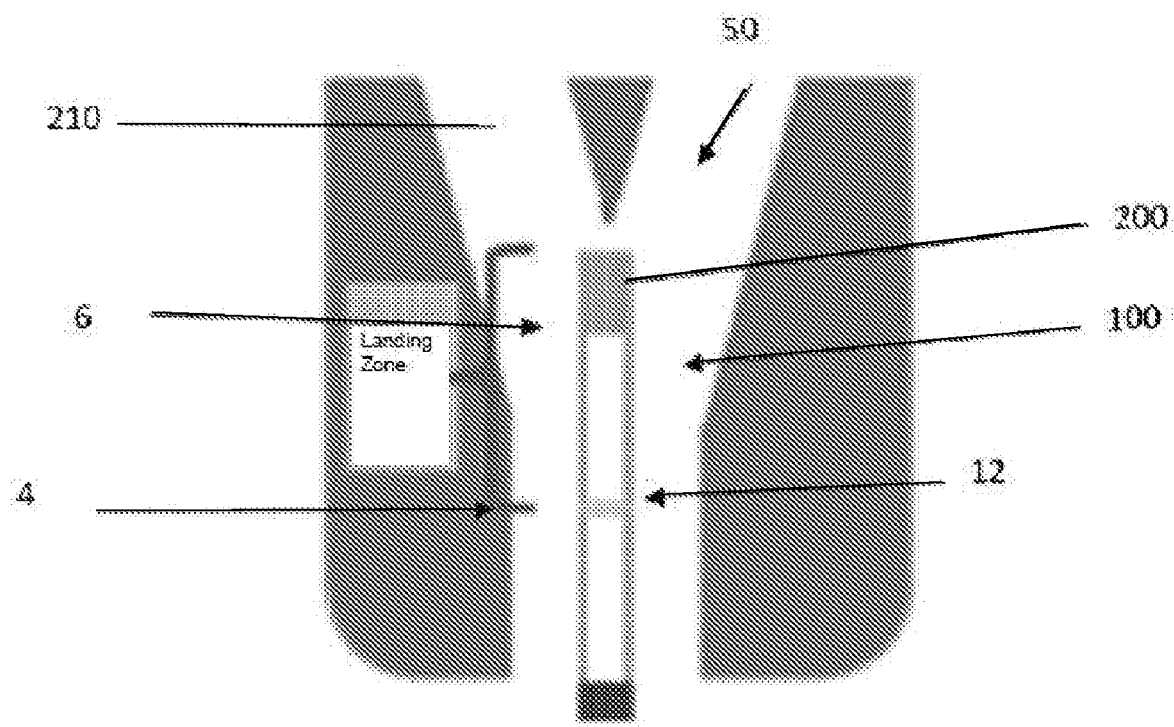
FIG. 4B illustrates a plan view of a valve delivery catheter in the passageway of FIG. 4A.

FIG. 4B illustrates a retracted 50 valve 100 inside a valve delivery catheter 200 that is being inserted into a passageway 210. The delivery catheter 200 has a seal area indicator 12 that is used to align the valve 100 with the seal area of the air way 210 that was measured by the valve planning tool (not shown). The seal area indicator 12 is located at the proximal end 4 of the valve 100. The delivery catheter 200 extend deeper into the airway 210 and beyond the distal end 6 of the valve 100 so that upon retraction of the delivery catheter 200, the valve 100 is deployed so that the seal area of the valve is aligned with where the seal area indicator 12 of the delivery catheter 100 was located.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Valve Planning Tool
4 Proximal end
6 Distal end
10 Balloon
12 Seal area indicator
14 Stem
16 Anchor indicator
18 Tangs
20 length indicator
50 Retracted State
52 Deployed state
100 valve
102 Anchor
104 Strut
106 membrane
108 Seal Area
200 Catheter
210 Airway
Θ Angle of Anchor Swing
D Diameter
L Length of valve planning tool
L' Length of valve

We claim:

1. A valve planning tool comprising:
   a. a stem having a distal end and a proximal end,
   b. an anchor indicator, including one or more tangs, located at the distal end, and
   c. a balloon located proximal of the anchor indicator, the balloon including:
      i. a retracted state and
      ii. a deployed state;
   wherein the balloon is inflatable from the retracted state to the deployed state and the balloon is substantially non-compliant so that the balloon is only inflatable to one size, wherein the one or more tangs are movable from a retracted state to a deployed state so that sweep of anchor swing can be visualized, and wherein a length from the one or more tangs to a seal area indicator of the balloon represents a length of a valve.

2. The valve planning tool of claim 1, wherein the balloon is inflatable with a compressible fluid.

3. The valve planning tool of claim 2, wherein the compressible fluid is air.

4. The valve planning tool of claim 1, wherein the balloon is made of polyether, a polyether block amide, polyamide, polyethylene terephthalate, a thermoplastic, a polyester, a minimally-stretchable plastic, a minimally-stretchable biocompatible plastic, a non-elastic plastic, a non-stretchable plastic, or a combination thereof.

5. The valve planning tool of claim 1, wherein the one or more tangs are static.

6. The valve planning tool of claim 1, wherein the valve planning tool includes a length indicator that extends from the one or more tangs to the distal end of the valve planning tool.

7. A kit comprising: two or more valve planning tools of claim 1,
   wherein a first valve planning tool has a seal area indicator diameter of 5 mm, an anchor indicator diameter of 8 mm, and a length of 10 mm; a second valve planning tool has a seal area indicator diameter of 6 mm, an anchor indicator diameter of 9 mm, and a length of 11 mm; a third valve planning tool has a seal area indicator diameter of 7 mm, an anchor indicator diameter of 10 mm, and a length of 12 mm; and a fourth valve planning tool has a seal area indicator diameter of 9 mm, an anchor indicator diameter of 12 mm, and a length of 12 mm.

8. The kit of claim 7, wherein a first valve planning tool of the two or more valve planning tools has a greater length, greater diameter, lesser length, lesser diameter, or a combination thereof than a second valve planning tool of the kit.

9. The kit of claim 7, wherein the kit includes four valve planning tools of different sizes.

10. A method comprising:
   a. compacting the valve planning tool of claim 1 into a retracted state, and
   b. inserting the valve planning tool into a working channel of a bronchoscope.

11. The method of claim 10, wherein the valve planning tool is inserted into a structure with an area of interest, and the valve planning tool is removed from the channel of a bronchoscope.

12. The method of claim 11, wherein the valve planning tool is inflated so that the valve planning tool moves from the retracted state to a deployed state within the area of interest, and the valve planning tool is compared to the structure to determine if the structure is larger or smaller than the structure.

13. The method of claim 12, wherein the method is repeated with a larger or a smaller valve planning tool if the structure is larger or smaller than the valve planning tool.

* * * * *